United States Patent [19]

Murphy

[11] 4,137,910

[45] Feb. 6, 1979

[54] METHOD AND MEANS FOR MEASURING CARDIAC PUMPING PERFORMANCE OF LEFT VENTRICLE

[76] Inventor: Donald H. Murphy, 14 Foster Pl., Sea Cliff, N.Y. 11579

[21] Appl. No.: 728,207

[22] Filed: Sep. 30, 1976

[51] Int. Cl.$^2$ .............................................. A61B 5/02
[52] U.S. Cl. .............................................. 128/2.05 R
[58] Field of Search ..................... 128/2.05 D, 2.05 E, 128/2.05 F, 2.05 P, 2.05 Q, 2.05 R, 2.05 V

[56] References Cited

U.S. PATENT DOCUMENTS

| | | | |
|---|---|---|---|
| 3,154,067 | 10/1964 | Stgnstrom et al. | 128/2.05 P |
| 3,267,932 | 8/1966 | Valliere | 128/2.05 D |
| 3,361,128 | 1/1968 | Colman | 128/2.05 P |
| 3,920,004 | 11/1975 | Nakayama | 128/2.05 V X |
| 3,996,925 | 12/1976 | Djordjevich | 128/2.05 N |
| 4,023,563 | 5/1977 | Reynolds et al. | 128/2.05 R |
| 4,038,976 | 8/1977 | Hardy et al. | 128/2.05 P |

OTHER PUBLICATIONS

George et al., "Medical Research Engineering" Fourth Quarter, 1967, pp. 21-24.

*Primary Examiner*—William E. Kamm
*Attorney, Agent, or Firm*—Edward H. Loveman

[57] ABSTRACT

A method and system for measuring and monitoring the dynamics of left ventricular contraction by analyzing the signals from an electrocardiogram and signals corresponding to either an invasive aortic pressure pulse (obtained during catherization) or a non-invasive carotid arterial pulse (measured with a piezoelectric crystal). The pressure pulses are differentiated and amplified to produce data indicative of systolic blood flow. This blood flow data is then integrated during the ejection period in synchronism with pulses derived from the electrocardiogram to produce data indicative of the ejected stroke volume. This per beat volumetric data is further integrated over a uniform one minute time interval to yield cardiac output information. The differentiated pressure pulses are further differentiated and amplified to obtain data indicative of the left ventricular forces inparted to the blood flow during systole.

11 Claims, 1 Drawing Figure

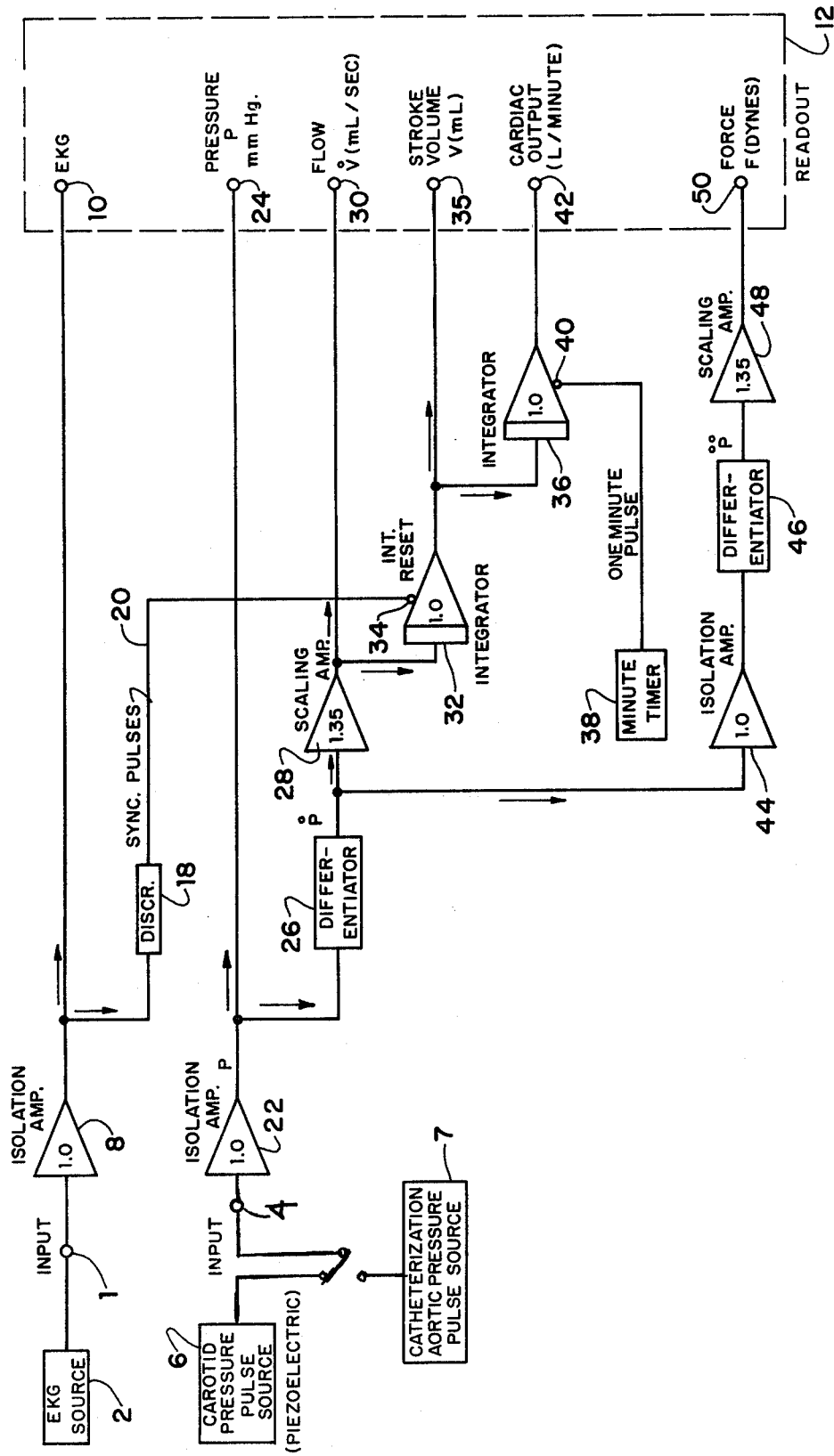

METHOD AND MEANS FOR MEASURING CARDIAC PUMPING PERFORMANCE OF LEFT VENTRICLE

This invention relates to the art of cardiac measuring means and more particularly concerns a method and means for measuring cardiac pumping performance of the left ventricle.

Much information relative to the dynamics of left ventricular contraction is implicit in the contour of the aortic pressure pulse. A linear time domain analysis of the arotic pressure wave indicates that it contains information relative to the flow of blood during systole, which heretofore could only be measured through electromagnetic flow meter techniques requiring thoracotomy. In addition, the arotic pressure wave form contains information relative to the left ventricular force which initiates flow (the isometric force of contraction) and that force which sustains flow throughout the ejection period (the isotonic force of contraction). These parameters heretofore could not be measured by any technique. If data on all of these variables were available to catherization laboratory, prior to coronary arteriography and left ventricular angiography, it would minimize mortality risks and significantly aid in the overall performance evaluation of the left ventricle.

The first time derivative of aortic pressure $\dot{P} = dp/dt$ contains information relative to the magnitude of systolic flow $\dot{V} = dv/dt$ and those parameters which modify flow.

If the time rate change of pressure $\dot{P}$ expressed in units of (mm Hg/sec) is multiplied by the constant 1.3534, the resulting product is flow $\dot{V}$ measured in units of milliliters per second (ml/sec)

$$\dot{V} = 1.3534 \, \dot{P} \text{ (ml/sec)}$$

If this pressure-derived flow is integrated with respect to time throughout the ejection period, $\gamma$, the resulting quantity is the stroke volume $\Delta V$ delivered during ventricular systole:

$$\Delta V = \int_0^\gamma \dot{V} \, dt = 1.3534 \int_0^\gamma \dot{P} \, dt \text{ (ml)}$$

If the stroke volume is multiplied by the heart rate (HR), the resulting product is equal to the cardiac output in liters per minute in accordance with its definition:

$$C.O. = \Delta V \times HR \left( \frac{\text{liters}}{\text{minute}} \right)$$

The second time derivative of aortic pressure $$\ddot{P} = \frac{d^2 P}{dt^2}$$

contains information relative to the magnitude of those ventricular forces which initiate and maintain the flow of systole (the isometric and isotonic forces respectively), and to those elastic forces due to radial information of the aortic root which damp this flow.

If the second time derivative of aortic pressure $\ddot{P}$ (expressed in units of (mm Hg/sec$^2$) is multiplied by the constant 1.3534, the resulting product is force F measured in units of dynes:

$$F = 1.3534 \, \ddot{P} \text{ dynes}$$

The contour of the carotid pulse is analogous to that of aortic pressure, and hence the respective time derivatives of the carotid pulse contain information with respect to flow ($\dot{V}$), stroke volume ($\Delta V$), cardiac output (C.O.), and ventricular Force (F) — all on a non-invasive basis. The manner in which the carotid pulse has heretofore been measured, however, is inadequate to faithfully reproduce the aortic pressure pulse, since instrumentation limitations result waveform distortion.

In accordance with the invention, the carotid pressure pulse is obtained from a piezoelectric crystal affixed to a Velcro ® type lock strap encompassing a patient's neck and is positioned directly over the carotid artery. Minimum contact pressure is maintained by the crystal, which produces an analog voltage proportional to the radial excursion of the arterial wall. With this technique the carotid pulse reproduces all frequency components in the aortic pressure contour in excess of 2 cycles per second (Hz).

Since the lowest frequency component of interest is in the order of 2.5 cycles per second, and the highest frequency component less than 40 cycles per second, there exists a high degree of assurance that the information detected at the cartoid artery exactly reproduces that at the aortic root.

It is, therefore a principal object of the present invention to provide means for determining the pumping performance parameters of the patient's left ventricle non-invasively by monitoring the carotid pulse.

Another object of the present invention is to provide means for measuring externally of a patient's body the magnitude of systolic flow and those parameters which modify flow.

A further object of the present invention is to provide means for determining externally of a patient's body the magnitude of those ventricular forces which initiate and maintain the flow of the systole, i.e., the isometric and isotonic forces respectively.

Still another object of the present invention is to provide means whereby the contour of the carotid pulse can be measured and analyzed non-invasively, i.e. externally of the body to provide information with respect to ventricular flow, stroke volume, cardiac output and ventricular force.

Yet another object of the present invention is to provide a method and system for measuring and monitoring the dynamics of left ventricular contraction by analyzing an invasive aortic pressure pulse obtained from catherization.

These and other objects and many of the attendant advantages of this invention will be readily appreciated as the same becomes better understood by reference to the following detailed description when considered in connection with the accompanying drawing in which:

The FIGURE is a functional schematic diagram of a system embodying the invention.

Referring now to the drawing, there is illustrated a system having one input to which is fed electrocardiographic signals obtained from an electrocardiograph 2 applied to a patient's body. To another system input 4, aortic pressure data is supplied from either a catherization source 7 or from the carotid artery pressure pulse source 6. The carotid pressure pulse source 6, is a piezoelectric crystal juxtaposed to a patient's carotid artery. It will be understood that both the EKG and the carotid pressure pulse signals or data are obtained simultaneously from the body of a patient by means external of i.e. non-invasive of the patient's body. The EKG input is applied via an isolation amplifier 8 to an output 10 of a readout apparatus 12 which can provide visual readout display as well as graphic output. The isolation amplifier 8 has unity (1.0) amplification to serve as a buffer between the input 1 and the output 10. The EKG input is also applied via the amplifier 8 to a discriminator 18 to produce syncronized pulses at a discriminator output line 20.

The pressure pulse data at input 4 is applied via another isolation amplifier 22 having unity (1.0) amplification to a readout output 24 where data indicating pressure P in millimeters of mercury (mm Hg) is displayed. The pressure pulse data is also applied to a differentiator 26 to produce data indicative of the first time derivative ($\dot{P}$) of the pressure pulse. The output from the differentiator 26 is applied via a scaling amplifier 28 having an amplification of 1.35 to a readout output 30. The data appearing at output 30 indicates ventricular flow $\dot{V}$ in milliliters/per second (ml/sec).

The output from the scaling amplifier 28 is also applied to the input of an integrator 32. The synchronized pulses derived from the discriminator 18 are applied to a reset input 34 of the integrator 32. The output from the integrator 32 is applied to a readout output 35. The data at output 35 indicates stroke volume $\Delta V$ in milliliters (ml).

The output from integrator 32 is applied to the input of another integrator 36. One minute pulses are applied by a timer 38 to reset input 40 of the integrator 36. The output from the integrator 36 is applied to a readout output 42. The data at this output indicates cardiac output in liters per minute (l/min).

The output from the differentiator 26 is further applied via an isolation amplifier 44 having unity amplification to a differentiator 46 to produce data corresponding to the second time derivative ($\ddot{P}$) of pressure pulse. The output from the differentiator 46 is applied via a scaling amplifier 48 having 1.35 amplification to a readout output 50, where the data indicates force F in dynes.

The readout apparatus 12 provides both a visual display and graphic record of the several readout outputs.

It will be apparent from the preceding description and analysis that if desired, the performance of a patient's left ventricle can be both measured and monitored by means entirely external of the patient's body. The left ventricular force which initiates flow and the force of contraction which sustains flow are both simultaneously measured. The system is readily assembled using electronic components commercially available, or easily constructed by known techniques. Although the system described has an analog format, it can alternatively be instrumented by using digital rather than analog techniques.

It should be understood that the foregoing relates to only a preferred embodiment of the present invention which has been by way of example only and that it is intended to cover all changes and modifications of the examples of the invention herein chosen for the purposes of the disclosure, which do not constitute departures from the spirit and scope of the invention.

The invention claimed is:

1. A system for measuring and monitoring the pumping performance of left ventricular contraction during systole of a patient's heart, comprising:
   pressure responsive means for deriving aortic pressure signals from a patient's body which are caused by the ejection of said left ventricle;
   differentiator means in circuit with said pressure responsive means for differentiating said pressure pulse signals; and
   amplifier means in circuit with said differentiator means for amplifying said differentiated pressure pulse signals to obtain data indicative of the blood flow from said patient's left ventricle during systole; and
   display means connected to said amplifier means for indicating said pumping performance of left ventricle contraction.
2. A system as defined in claim 1, further comprising:
   electrocardiographic means for obtaining an electrocardiogram of the patient;
   discriminator means in circuit with said electrocardiographic signal means for deriving synchronized pulses from said electrocardiogram; and
   integrator means in circuit with said amplifier means and said discriminator means to obtain stroke volume data indicative of the volume of blood flow per stroke from said patient's left ventricle during systole; and
   said integrator means being connected to said display means for indicating said stroke volume data.
3. A system as defined in claim 2, further comprising:
   time means for producing uniform one minute time pulses; and
   other integrator means in circuit with said timer means and the first named integrator means to produce cardiac output data indicative of the total blood flow per minute from the left ventricle of the patient's heart during each minute; and
   said other integrator means coupled to said display means for indicating blood flow per minute.
4. A system as defined in claim 1, further comprising:
   another differentiator means in circuit with the first named differentiator means to obtain data indicative of the second derivative of said pressure pulses; and
   other amplifier means in circuit with said other differentiator means to provide signal data indicative of the force with which blood flows from the patient's left ventricle during systole;
   said other amplifier means connected to said display means to indicate the force with which blood flows from the patient's left ventricle during systole.
5. A system as defined in claim 1, wherein said pressure responsive means comprises a piezoelectric device.
6. A system as defined in claim 1, wherein said pressure responsive means comprises a catheter pressure device.
7. A method for measuring and monitoring the pumping performance of left ventricular contraction during systole of a patient's heart, comprising:
   deriving aortic pressure pulse signals caused by contraction of the left ventricle;
   differentiating said pressure pulses; and
   amplifying the differentiated pressure pulses to obtain data indicative of the blood flow from the patient's left ventricle during systole;

displaying the amplified pressure pulses to measure and monitor the pumping performance of left ventricle contraction.

8. A method as defined in claim 7, further comprising:
obtaining an electrocardiogram of the patient while deriving said pressure pulses;
discriminating the electrocardiogram for deriving synchronous pulses therefrom; and
integrating said flow data in synchronism with said synchronous pulses to obtain stroke volume data indicative of the volume of blood per stroke from the patient's left ventricle during systole.

9. A method as defined in claim 8, further comprising:
creating uniformly timed pulses; and
integrating said stroke volume data in synchronism with said uniformly timed pulses to produce cardiac output data indicative of the total per minute flow of blood from the left ventricle of the patient's heart during each time interval.

10. A method as defined in claim 8, further comprising:
differentiating the differentiated pressure pulses to obtain further pulses indicative of the second derivative of said pressure pulses; and
amplifying said further pulses to obtain signal data indicative of the force with which blood flows from the patient's left ventricle during systole.

11. A method as defined in claim 7, further comprising:
differentiating the differentiated pressure pulses to obtain further pulses indicative of the second derivative of said pressure pulses; and
amplifying said further pulses to obtain signal data indicative of the force with which blood flows from the patient's left ventricle during systole.

* * * * *